United States Patent [19]
Hirano et al.

[11] Patent Number: 5,223,519
[45] Date of Patent: Jun. 29, 1993

[54] 4-HYDROXYPYRIDINE DERIVATIVES, USEFUL FOR TREATING CIRCULATORY DISEASES

[75] Inventors: Shin-ichi Hirano, Chigasaki; Yoshio Watanabe, Fujisawa; Kaichiro Kominato, Yamato; Naoki Agata, Fujisawa; Yutaka Hara, Yokohama; Norio Shibamoto, Chigasaki; Takeo Yoshioka, Ayase; Tomoyuki Kioka; Hiroshi Iguchi, both of Yokohama; Masataka Shirai, Tokyo; Hiroshi Tone, Yokohama; Rokuro Okamoto, Fujisawa, all of Japan

[73] Assignee: Mercian Corporation, Tokyo, Japan

[21] Appl. No.: 830,202

[22] Filed: Dec. 13, 1991

[30] Foreign Application Priority Data

Dec. 14, 1990 [JP] Japan .................................. 2-410526

[51] Int. Cl.$^5$ .................... A61K 31/44; C07D 213/69; C12N 1/20
[52] U.S. Cl. .................................... 514/348; 546/296; 435/253.5
[58] Field of Search ........................ 546/296; 514/348

[56] References Cited
PUBLICATIONS

Yano, et al., "Actinopyrones A,B and C, new physiologically active substances. II. Physicochemical properties and chemical structures", Chemical Abstracts, vol. 105, No. 25, Dec. 1986, p. 747, col. 1, 226123r.

Jansen, et al., "Revised stereochemistry for pipericidin A$_1$", Chemical Abstracts, vol. 100, No. 15, Apr. 1984, p. 561, col. 2, 120743z.

Yoshida, et al., "The structural revision of pipericiden A by combination of CMR spectroscopic and biosynthetic studies", Chemical Abstracts, vol. 87, No. 5, Aug. 1977, p. 497, col. 1, 39240z.

*Primary Examiner*—Alan L. Rotman
*Attorney, Agent, or Firm*—Cushman, Darby & Cushman

[57] ABSTRACT

4-Hydroxypyridine derivative represented by the following formula

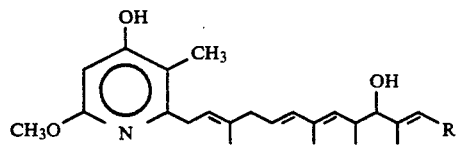

wherein R represents a methyl group or an isopropyl group, and the method for preparing the derivative comprising the step of cultivating a strain belonging to *Streptomyces karnatakensis* are disclosed. Also disclosed are the pharmaceutical composition comprising the same and a method for treating circulatory diseases comprising the step of administering said compound to a patient.

4 Claims, 4 Drawing Sheets

4-HYDROXYPYRIDINE DERIVATIVES, USEFUL FOR TREATING CIRCULATORY DISEASES

BACKGROUND OF THE INVENTION

1. Field of the Invention

The present invention relates to a novel 4-hydroxypyridine derivative useful as a vasodilator and vasodepressor, a method for preparing the 4-hydroxypyridine derivative, and a pharmaceutical composition comprising the derivative.

More specifically, the present invention relates to a 4-hydroxypyridine derivative represented by the following formula (I):

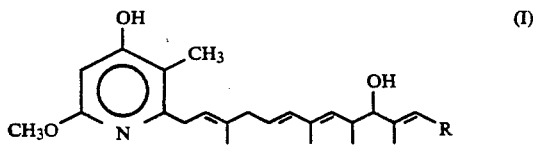

wherein R represents a methyl group or an isopropyl group. The present invention also relates to a method for preparing the 4-hydroxypyridine derivative comprising the step of cultivating a microorganism, a pharmaceutical composition comprising an effective amount of the derivative, and a method for treating circulatory diseases comprising the step of administering the derivative.

2. Description of the Related Art

Yoshida et al. (Argic. Biol. Chem., 41: 849–862, 1977) discloses a series of Piericidins represented by the following formulas:

Piericidin A:

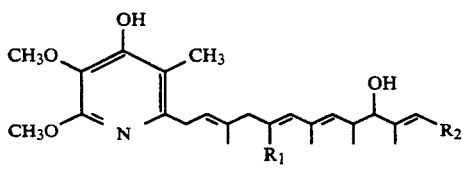

Piericidin B:

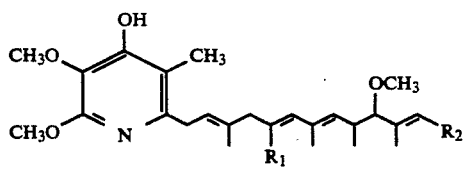

Piericidin C:

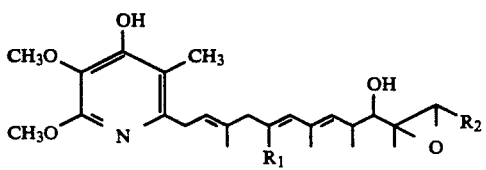

Piericidin D:

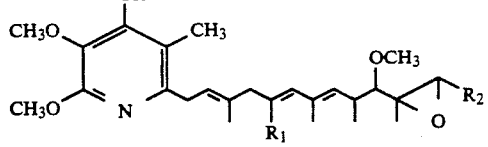

treatment of circulatory diseases.

Thus, in accordance with the above objects, the present invention provides a novel 4-hydroxypyridine derivative represented by the following formula:

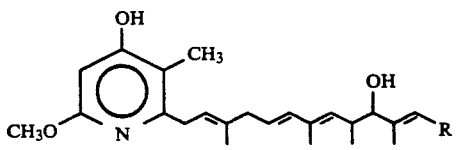

wherein R represents a methyl group or an isopropyl group.

In accordance with another embodiment of the present invention, there is provided a method for preparing the novel 4-hydroxypyridine derivatives which comprises the steps of cultivating a strain belonging to *Streptomyces karnatakensis* which can produce said compound.

In accordance with further embodiments, the present invention provides a pharmaceutical composition comprising an effective amount of the 4-hydroxypyridine derivative, and a method for treating circulatory diseases which comprises the step of administering to a patient an effective amount of said 4-hydroxypyridine derivative.

Further objects, features and advantages of the present invention will become apparent from the Description of the Preferred Embodiments which follows, when read in light of the accompanying Examples. methoxyl group in thir molecules. Actinopyrones are also not structural analogues of the 4-hydroxypyridine compounds of the present invention, because Actinopyrone is characterized as having a pyrone nucleous, while the compounds of the present invention have a pyridine ring structure.

SUMMARY OF THE INVENTION

An object of the present invention is to provide novel 4-hydroxypyridine compounds which can be useful as vasodilators and vasodepressing agents.

Another object of the present invention is to provide a method for preparing the 4-hydroxypyridine compounds.

Further objects of the present invention are to provide a pharmaceutical composition comprising an effective amount of the 4-hydroxypyridine compound, and a method for treating circulatory diseases comprising the step of administering the 4-hydroxypyridine compound or the pharmaceutical composition.

Vasodilating activity can be induced by a variety of physiological and biological factors, and thus, various types of compounds have been screened for vasodilating activity. The inventors of the present invention have conducted extensive screening to achieve the foregoing objects and found that the objects can be effectively attained by providing novel 4-hydroxypyridine compound represented by the above-described formula (I). The inventors have also found that the compounds of the present invention having vasodilating activity and vasodepressor activity are useful for the wherein R₁ represents a hydrogen atom or a methyl group, and R₂ represents a methyl group or an isopropyl group.

Yano et al. (J. Antibiotics 39: 38–43, 1986) discloses series of Actinopyrones represented by the following formula:

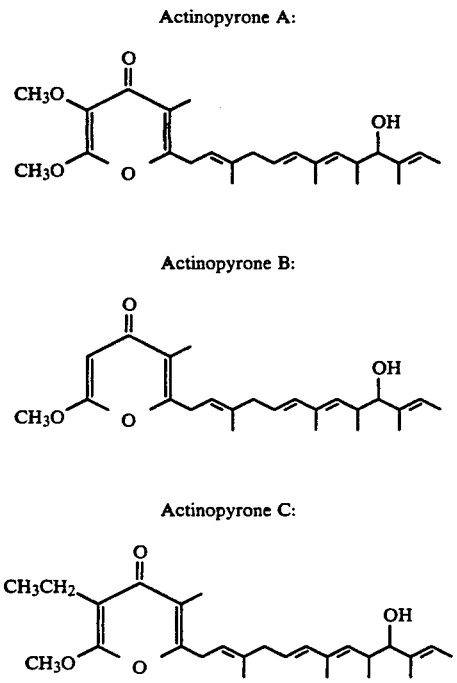

The physicochemical properties of Piericidins and Actinopyrones are similar to those of the 4-hydroxypyridine compounds of the present invention represented by the above-described formula (I). However, the 4-hydroxypyridine compounds of the present invention structually differ from Piericidins, because each Piericidine has two or three methoxyl substituents in its molecule, while both of the compounds of the present invention have only one

DETAILED DESCRIPTION OF THE PREFERRED EMBODIMENTS

The present invention provides a novel 4-hydroxypyridine derivative represented by the above-described formula (I), wherein R represents a methyl group or an isopropyl group. It should be recognized that the tautomeric isomers of the above-defined compounds of the present invention fall within the scope of the present invention, which are represented by the following formula (II):

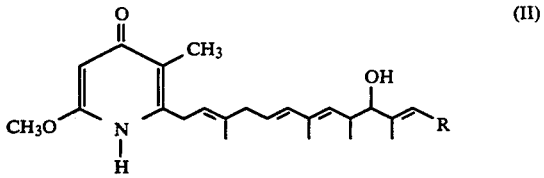

wherein R represents a methyl group or an isopropyl group.

Figure 1:
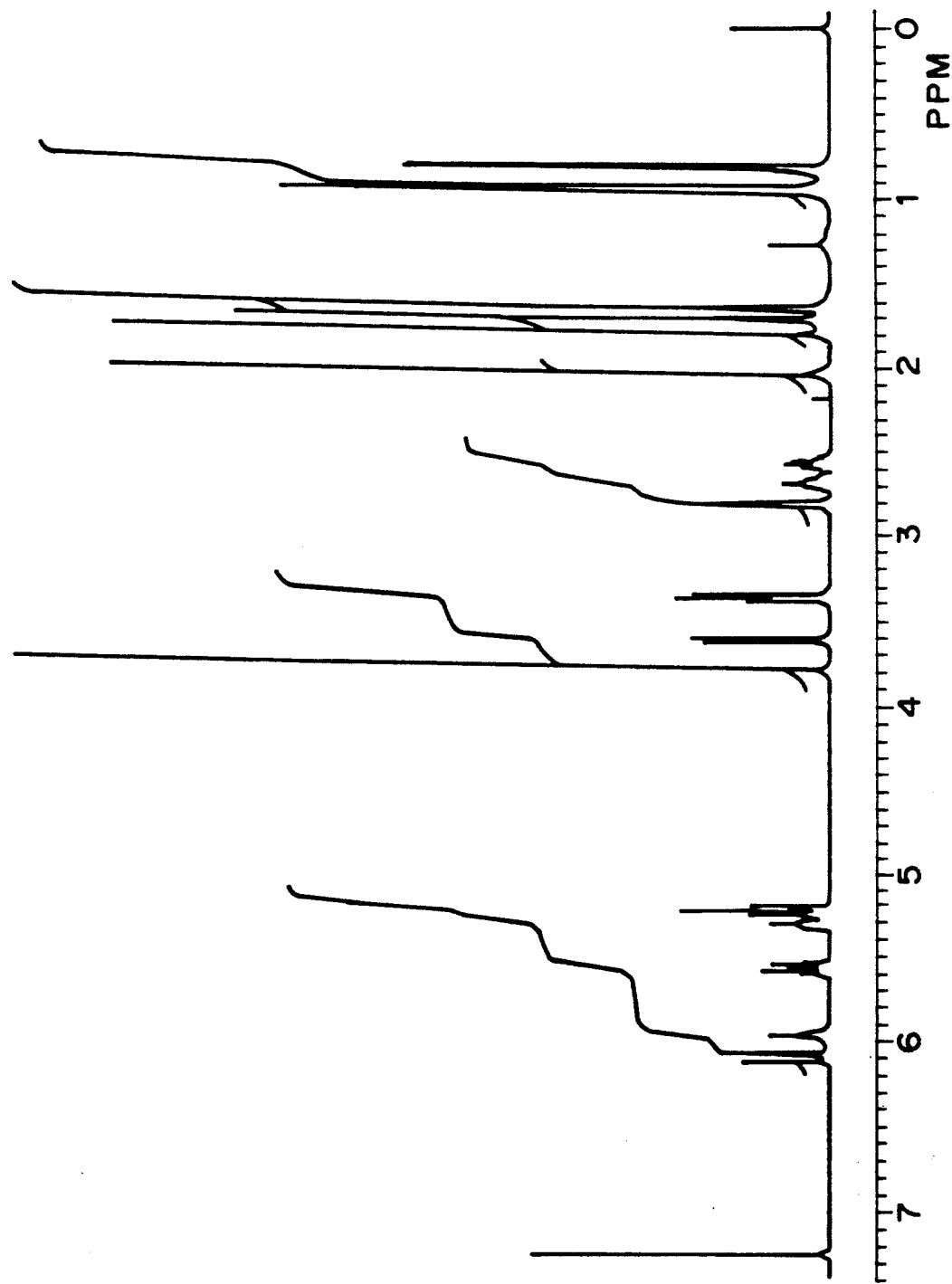
FIG. 1 shows a 400 MHz $^1$H NMR spectrum of the compound of the present invention wherein R is a isopropyl group.
Figure 2:
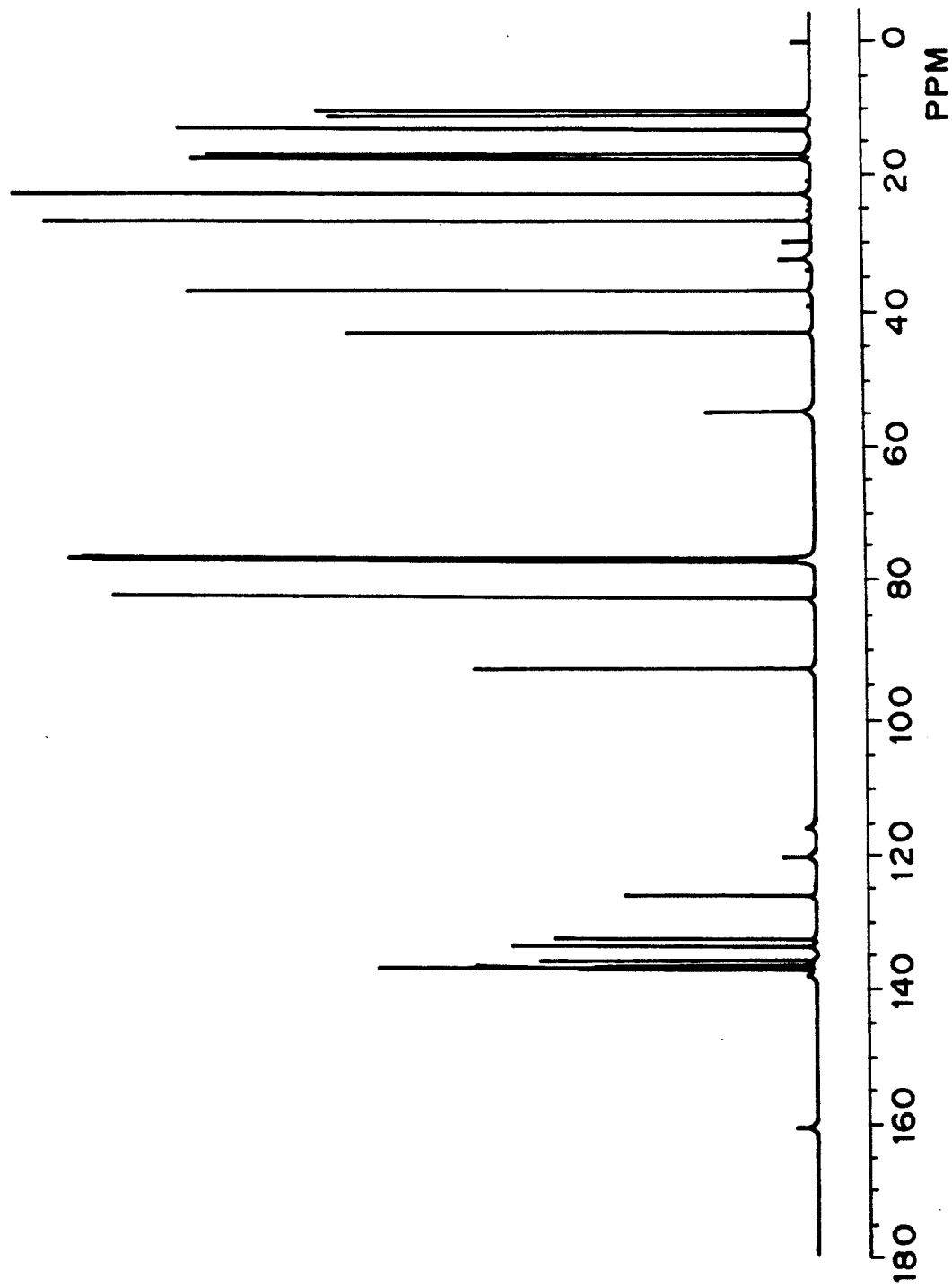
FIG. 2 shows a 100 MHz $^{13}$C NMR spectrum of the compound of the present invention wherein R is a isopropyl group.

The compound of the present invention wherein R is an isopropyl group (hereinafter also referred to as Mer-A2026A) is a yellow oil which is soluble in commonly available organic solvents and insoluble in water. This compound has the molecular weight of 413 ($C_{26}H_{39}NO_3$) and the following physicochemical properties. The mass spectrum (SIMS) gives m/z at 414 [(M+H)+]. Specific rotation is (solvent: methanol, c 1.85 at 22° C.):[α]$_D$= −12.3°. The ultraviolet absorption spectrum (solvent: methanol) shows maxima at 238.5 nm (ε37400) and 223.2 nm(ε33700). The infra-red absorption spectrum (solvent: chloroform) gives peaks at 3350, 2950, 2860, 1635, 1590, 1520, 1460, 1390, and 970 cm$^{-1}$. The 400 MHz proton magnetic resonance spectrum as shown in FIG. 1 of the accompanying drawing shows the following signals (δppm; in CDCl₃; TMS as internal standard): 0.82(3H,d,J=6.6Hz), 0.94(3H,d,J=6.6Hz), 0.96(3H,d,J=6.6Hz), 1.64(3H,s), 1.71(3H,s), 1.79(3H,s), 2.03(3H,s), 2.55(1H,m), 2.67(1H,m), 2.81(2H,d,J=7.0Hz), 3.36(2H,d,J=7.0Hz), 3.61(1H,d,J=8.8Hz), 3.78(3H,s), 5.21(1H,d,J=9.5Hz), 5.24(1H,d,J=10.6Hz), 5.30(1H,brt,J=6.6Hz), 5.57(1H,td,J=7.0 and 15.4Hz), 5.96(1H,brs), and 6.09(1H,d,J=15.4Hz). The 100 MHz carbon magnetic resonance spectrum as shown in FIG. 2 of the accompanying drawing shows the following signals (δppm; in CDCl₃; the signal of the solvent at 77.0 ppm from TMS is used as a reference): 10.1(q), 10.8(q), 13.1(q), 16.5(q), 17.4(q), 22.7(q), 22.8(q), 26.8(d), 32.1(t), 36.9(d), 43.0(t), 54.6(q), 82.7(d), 92.4(d), 115.8(s), 120.1(d), 125.8(d), 132.4(s), 133.5(d), 135.6(s), 136.2(d), 136.9(d), 138.0(s), and 160.4(s).

Figure 3:
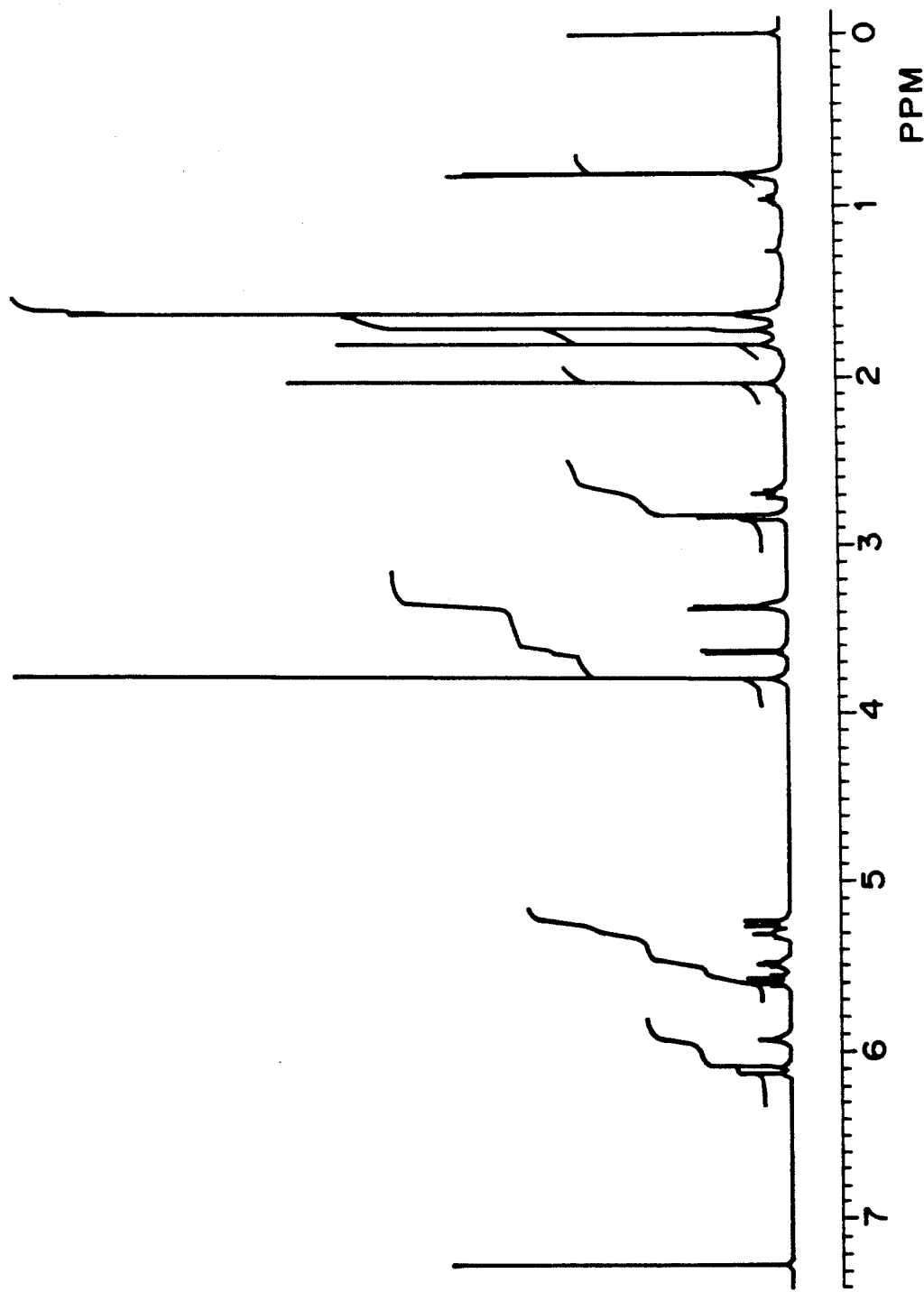
FIG. 3 shows a 400 MHz $^1$H NMR spectrum of the compound of the present invention wherein R is a methyl group.
Figure 4:
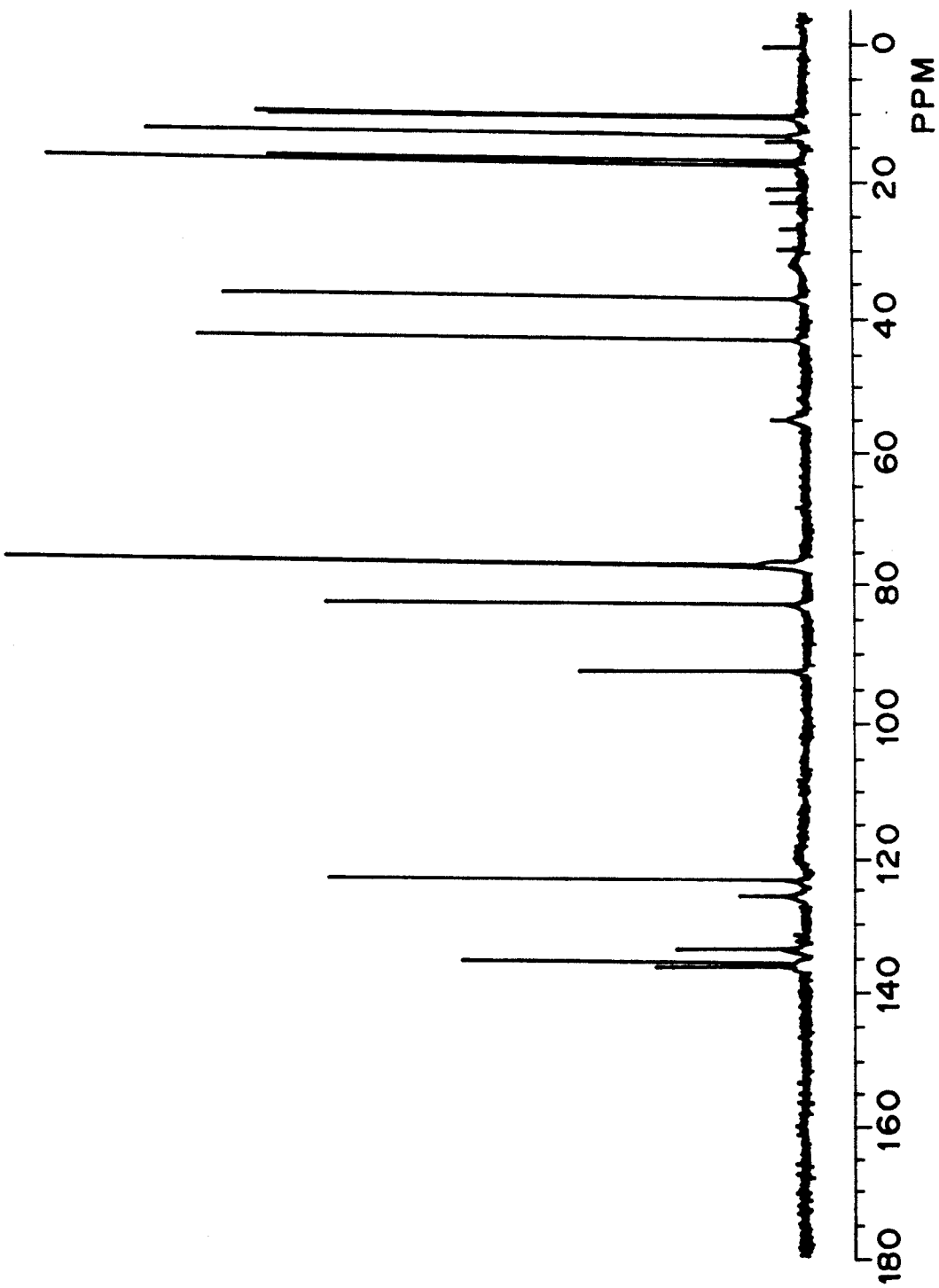
FIG. 4 shows a 100 MHz $^{13}$C NMR spectrum of the compound of the present invention wherein R is a methyl group.

The compound of the present invention wherein R is a methyl group (hereinafter in the specification, this compound can also be referred to as Mer-A2026B) is a yellow oil which is soluble in commonly available organic solvents and insoluble in water. This compound has the molecular weight of 385 ($C_{24}H_{35}NO_3$) and the following physicochemical properties. The mass spectrum (FAB) gives positive m/z at 386 [(M+H)+] and negative m/z at 384 [(M−H)+]. Specific rotation is (solvent methanol, c 0.36 at 24° C.):[α]$_D$= −1.07°. The ultra-violet absorption spectrum (solvent: methanol) shows the maxima at 238.4 nm (ε37600) and 223.2 nm(ε33400). The infra-red absorption spectrum (solvent chloroform) gives peaks at 3340, 2920, 2860, 1635, 1590, 1520, 1460, 1385, and 970 cm$^{-1}$. The 400 MHz proton magnetic resonance spectrum as shown in FIG. 3 of the accompanying drawing shows the following signals (δppm; in CDCl₃; TMS as internal standard): 0.81(3H,d,J=6.6Hz), 1.63(3H,dd,J=7.0 and 1.1Hz), 1.64(3H,s), 1.72(3H,d,J=1.1Hz), 1.81(3H,d,J=1.1Hz), 2.03(3H,s), 2.69(1H,m), 2.83(2H,d,J=7.0Hz), 3.36(2H,d,J=7.0Hz), 3.64(1H,d,J=9.2Hz), 3.79(3H,s), 5.24(1H,d,J=9.9Hz), 5.32(1H,brt,J=7.0Hz), 5.49(1H,m), 5.58(1H,td,J=7.0 and 15.4Hz), 5.93(1H,brs), and 6.10(1H,d,J=15.4Hz). The 100 MHz carbon magnetic resonance spectrum as shown in FIG. 4 of the accompanying drawing shows the following signals (δppm; in CDCl$_3$; the signal of the solvent at 77.0 ppm from TMS is used as a reference): 10.1(q), 10.6(q), 13.1(q), 16.6(q), 17.4(q), 36.9(d), 43.0(t), 54.6(q), 82.8(d), 92.4(d), 123.5(d), 125.8(d), 133.6(d), 135.6(s), 135.7(s), and 136.3(d).

In accordance with another embodiment of the present invention, there is provided a method for preparing Mer-A2026 selected from the group of Mer-A2026A and Mer-A2026B which comprises the steps of cultivating a Mer-A2026-producing strain belonging to *Streptomyces karnatakensis* in an aqueous nutrient medium, and recovering the Mer-A2026 from the culture.

An example of the Mer-A2026-producing microorganisms useful for the method for preparing Mer-A2026 is a newly discovered species of actinomycetes isolated from a soil sample collected in the riverside of Hikichi river, Fujisawa city, Kanagawa, Japan in 1989 (hereinafter referred to as *Streptomyces karnatakensis* Me2108).

*Streptomyces karnatakensis* Me2108 shows the following morphological, cultural and physiological characteristics:

1. Morphological characteristics

The aerial hyphae of the cultured strain is well branched and the top of the aerial hyphae is closed spiral. After growing up, it becomes divided and forms a spiral chain of conidia. The size of spherical or elliptical conidium is about 1.0×1.0−1.2 μm. The surface of the conidium is hairy with a lot of spines. No flagellum is observed.

2. Cultural characteristics

The strain has the following cultural characteristics when grown On media as described below at 30° C. The color of the surface of colony is indicated according to the symbols described in color Harmony Manual.

(i) Yeast malt agar: Good growth with a lot of epiphytal aerial hyphae and conidium. The color of the surface of colony is faint gray reddish brown (5fe). Melanoid pigment and soluble pigment are not observed.

(ii) Tripton yeast agar: Moderate growth with slight aerial hyphae formation. The color of the surface of colony is white (a). Very small amount of or almost no epiphytal conidium is observed. Melanoid pigment and soluble pigment are not observed.

3. Carbon source utilization

The carbon source utilizing pattern according to PridhamGottlieb medium are summarized in the following Table 1:

TABLE 1

| Source of carbon | Growth |
|---|---|
| L-Arabinose | − |
| D-Xylose | − |
| D-Glucose | + |
| D-Fructose | − |
| Sucrose | − |
| Inositol | − |
| L-Rhamnose | − |
| Raffinose | − |
| D-Mannitol | − |

−: Not utilized
+: Utilized

4. Physiological characteristics

L,L-Diaminopimelic acid is observed as one of the components of cell wall when cell wall is analyzed by cellulose thin layer chromatography after hydrolyzation. No particular pattern of sugar components is observed. The type of cell wall is classified as Type I.

From the foregoing bacterial characteristics, it is apparent that the bacterial strain Me2108 belongs to Streptomyces. Further, these bacterial characteristics are identical with those of *Streptomyces karnatakensis* published and authorized by International Streptomyces Project (ISP), except that the utilization of fructose is described as being±in the ISP publication. The inventors of the present invention thus concluded that the bacterial strain Me2108 belongs to *Streptomyces karnatakensis*. This strain has been deposited at Fermentation Research Institute, Agency of Industrial Science and Technology, 1-1-3, Higashi, Tsukuba, Ibaraki 305, Japan, under the access number FERM BP-3583. The microorganism has been deposited under the Budapest Treaty and all restrictions to access will be removed upon the grant of a patent.

It is to be understood that, for the preparation of MerA2026, the present invention is not limited to the use of the particular organism described herein, which is given for illustrative purpose. This invention also may include the use of mutants produced from the described organism by conventional means, such as X-rays, ultraviolet radiation, nitrogen mustard, or the like.

The Mer-A2026 can be prepared by cultivating a strain which belongs to *Streptomyces karnatakensis* and produces Mer-A2026 in a medium containing assimilable nutrients such as the sources of carbon and nitrogen, and inorganic salts. Any known nutrients used for the cultivation of actinomyces may be utilized in the medium.

Examples of the source of carbon in the medium include, for example, glucose, sucrose, starch syrup, dextrin, starch, glycerol, molasses, animal oil, or vegetable oil. Examples of the source of nitrogen atom include, for example, soybean meal, wheatgerm meal, corn steep liquor, cottonseed meal, meat extract, peptone, yeast extract, ammonium sulfate, sodium nitrate, and urea. These carbon and nitrogen sources may preferably be used in combination. If desired, mineral salts may be added to the medium. Examples of the salts include, for example, sodium salts, potassium salts, calcium salts, magnesium salts, cobalt salts, chlorides, phosphates, or sulfates. Furthermore, appropriate organic or inorganic materials, which enhance the growth of bacteria and the production of Mer-A2026 in the medium, may be added to the medium.

For the production of Mer-A2026, aerobic cultivation, preferably, submerged aerobic cultivation may be used. The fermentation may be conducted at a temperature of from 15° to 30° C., generally at 28° C. The productivity of Mer-A2026 generally depends on the cultural medium and the conditions of cultivation, however, the cumulative amount of Mer-A2026 will generally reach a maximum in about two to ten days where shaking culture or tank cultivation is carried out. The 4-hydroxypyridine derivative Mer-A2026A and Me-rA2026B can be recovered from the culture medium and purified after the maximum amount of Mer-A2026A and Mer-A2026B is cumulated.

The recovery and purification of the 4-hydroxypyridine derivative Mer-A2026A and Mer-A2026B can be conducted by conventional means utilizing the physicochemical properties of these compounds. Such separation methods include, for example, extraction with solvent, adsorption column chromatography, gel filtration, precipitation, and combinations thereof. For example, the 4-hydroxypyridine derivative of the present invention, accumulated mostly in the cultured broth, can be extracted in an organic layer using a water-immiscible organic solvent such as butanol. Partial purification can be conducted by the steps of, for example, evaporating the solvent, dissolving the residue in an organic solvent, removing impurities as precipitates by adding ether to the solution, filtering the solution to obtain filtrate containing Mer-A2026, and evaporating the solvent to afford a dark brown oily residue containing Mer-A2026A and/or Mer-A2026B.

Further purification of Mer-A2026A and/or Mer-A2026B can be conducted by applying the resulting residue on a chromatography column using an adsorbent such as, for example, Sephadex LH-20 (Pharmacia) or silica gel (such as Wakogel C-200 available from Wako Pure Chemicals, or Kieselgel 60 available from Merck).

In accordance with a further embodiment of the present invention, there is provided a pharmaceutical composition comprising an effective amount of the 4-hydroxypyridine derivative of the present invention together with a pharmaceutically-acceptable carrier or coating. The pharmaceutical composition is useful as a vasodilator and vasodepressor for the treatment of circulatory diseases including diseases of cardiovascular system. The following experimental results clearly demonstrate these pharmacological activities of the compounds of the present invention.

Vasodilating activity

Male Sprague-Dawley rats weighing 250-300 g were sacrificed by cervical dislocation and exsanguinated. The thoracic aorta was dissected out and helical strips, 2 mm wide and 10 mm long, were prepared. Each preparation was mounted in a 10 ml organ bath containing physiological saline solution (Krebs-Henzeleit solution, pH 7.4). The solution was gassed with 95% $O_2$- 5% $CO_2$ at 37° C. and a resting tension of 0.5 g was applied. Tissues were allowed to equilibrate for at least 60 minutes before the application of test substances. The developed tension was measured isometrically with a force-displacement transducer and recorded on pen-recorder. Tissues had been contracted with $10^{-7}$ M norepinephrine or isotonic 60 mM KCl and test substances were applied cumulatively.

As shown in Table 2, the potency of each test substance for the relaxation was expressed as $IC_{50}$ (concentration needed to induce a 50% decrease in norepinephrine - or KCl-induced contraction). Both Mer-A2026A and Mer-A2026B more greatly relaxed the aorta than papaverine which commonly used as a vasodilator.

TABLE 2

| Compound | $IC_{50}$ (M) | |
|---|---|---|
| | Norepinephrine | Isotonic KCl |
| Mer-A2026A | $2.0 \times 10^{-7}$ | $1.0 \times 10^{-6}$ |
| Mer-A2026B | $7.7 \times 10^{-7}$ | $4.0 \times 10^{-7}$ |
| Papaverine | $4.7 \times 10^{-6}$ | $1.7 \times 10^{-5}$ |

Depressor effect

Male spontaneously hypertensive rats (SHR rats), 25-31 weeks old, were anesthetized with 40 mg/kg of pentobarbital sodium injected intraperitoneally. For the measurement of blood pressure, a cannula was inserted into the left carotid artery and connected to a multipurpose polygraph through a pressure transducer. Each animal was allowed to equilibrate for at least 30 minutes before injection and test substances were injected into the femoral vein through a polyethylene tube.

As shown in Table 3, Mer-A2026A markedly prolonged the duration time and decreased the blood pressure. These results indicate that Mer-A2026A is an effective vasodepressor.

TABLE 3

| Compound | Dose (μg/kg) | Vasodepression | Duration time |
|---|---|---|---|
| Mer-A2026A | 10 | 3.6 | 0.2 |
| | 30 | 25.0 | 9.4 |
| | 100 | 47.7 | 24.5 |
| Papaverine | 1000 | 52.0 | 2.2 |

Toxicity

The acute toxicity of Mer-A2026A was determined in ICR male mice. Five mice were used at each dose. An intravenous injection of 500 μg/Kg sacrificed the one mouse, but at 250 μg/Kg all survived.

The compound of the present invention may be administered to a patient as a pharmaceutical composition such as a composition for oral administration, parenteral administration, or topical administration. The pharmaceutical composition may also be in the form of bathing agent. The pharmaceutical composition comprises an effective amount of the compound of the present invention together with a pharmaceutically-acceptable carrier or coating. The pharmaceutical composition is useful as vasodilator and vasodepressor for the treatment of circulatory diseases.

The pharmaceutical composition suitable for oral administration may be in a form of, for example, tablets, capsules, granules, or powder, which can be prepared by mixing 0.1 to 500 mg of the compound of the present invention with carriers such as, for example, lactose or starch, and formulating the mixture, if desired. The pharmaceutical composition suitable for oral administration may also be in a form of solution, syrup, or ampuled liquid medicine, which can be prepared by dissolving or suspending 0.1 to 500 mg of the compound of the present invention in an aqueous medium such as, for example, purified water or distilled water. The pharmaceutical composition suitable for parenteral administration may be an injection, which can be prepared by dissolving or suspending 0.1 to 20 mg of the compound of the present invention in an aqueous medium such as, for example, distilled water for injection. The pharmaceutical composition suitable for topical application may be a hair tonic or a hair grower which can be prepared as a tonic by using a solvent such as ethanol. The pharmaceutical composition suitable for topical application may also be a toiletry such as a bathing agent for comfortable bathing.

The dose of the pharmaceutical composition of the present invention for an adult patient may genarally be from about 10 to 30 mg per day for oral administration, which may be increased or decreased depending on the conditions of the patient to be treated.

The present invention will be further illustrated by the following Examples and Reference Examples. The Examples are given by way of illustration only and are not to be construed as limiting. It will be recognized by one ordinary skill in the art that the compound of the present invention described above can be prepared by various methods which may include any one of the steps of producing said compound by cultivating a microorganism in a medium, concentrating the culture, extracting the substances, and purifying said compounds. In Examples, all percentages are based on percents by weight unless otherwise specifically mentioned.

EXAMPLE

The inoculum medium had the following ingredients: 2.0% glycerol; 2.0% glucose; 2.0% soybean meal; 0.5% yeast extract; 0.25% sodium chloride; 0.32% calcium carbonate; and 0.2% of metal salt solution containing 0.25% copper sulfate, 0.25% manganese chloride, and 0.25% zinc sulfate. The production medium was the same as the inoculum medium except that 2.0% potato starch was used instead of 2.0% glycerol. An antifoaming agent (0.05%) was added to the culture medium for jar fermentation. The medium was adjusted to pH 7.4 before being sterilized.

The inoculum medium (50 ml) in a 500 ml Erlenmeyer flask was sterilized at 120° C. for 15 minutes. The medium was then inoculated with a loopful of the slant culture of Streptomyces karnatakensis Me2108. A shaking cultivation was carried out for three days at 28° C. to prepare a first-stage inoculum. The production medium (5 liter) was put into each three 10 liter jar fermentors and sterilized for 30 minutes at 120° C. To the production medium, each 100 ml of the first-stage inoculum was added and the medium was cultured with stirring (300 rpm) and aeration (1 vvm) at 28° C. for 4 days.

After the fermentation, the supernatant collected by centrifugation was extracted with 12 liter of butanol and the solvent was evaporated under a reduced pressure to give a residual dark-brown oil. The oil was dissolved in 200 ml of methanol, and then 800 ml of ether was added to precipitate impurities which were then removed by filtration. The filtrate was concentrated and the resulting residue was then dissolved in a small amount of methanol. The methanol solution was applied on a column of Sephadex LH-20 (400 ml), and fractions containing active substances were collected using methanol as an eluent. The fractions were concentrated to give residue containing active substances.

The residue was dissolved in chloroform-methanol (50:1), and the solution was applied to a column of 250 ml silica gel (Wakogel C-200). Fractions were obtained by using each 800 ml of chloroformmethanol (50:1), chloroform-methanol (20:1), and then chloroformmethanol (10:1) as eluents. The fractions eluted in chloroformmethanol (20:1) were collected and the solvent was evaporated. The resulting residue was then dissolved in a small volume of tolueneacetone (5:1) and the solution was applied on a column of 50 ml silica gel (Kieselgel 60, Merck). Fractions were obtained using each 150 ml of toluene-acetone (5:1), toluene-acetone (2:1), and then toluene-acetone (1:1) as eluents.

The fractions eluted in toluene-acetone (2:1) were collected and the resulting residue was applied on a preparative thin-layer chromatography (Kieselgel 60 F$_{254}$, Merck) using toluene-acetone (1:1) as a developer. Fractions at Rfs 0.53 and 0.51 having ultraviolet absorption were separately collected as Fraction A and Fraction B, respectively. Fraction B was again chromatographed under the same conditions described above for further purification. Fraction A and Fraction B were applied to a gel filtration using Sephadex LH-20 (100 ml) to afford Mer-A2026A (53.5 mg) and Mer-A2026B (9.9 mg), respectively.

One of ordinary skill in the art will recognize that improvements and modifications may be made while remaining within the scope and spirit of the present invention. The scope of the present invention is determined solely by the appended claims.

What is claimed is:

1. A 4-hydroxypyridine derivative represented by the following formula (I):

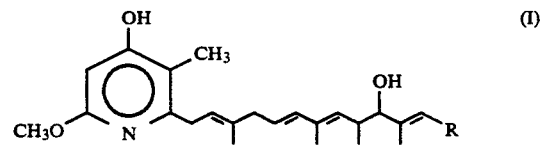

where in R represents a methyl group or an isopropyl group.

2. A method for treating circulatory diseases which comprises the step of administering to a mammal in need of said treatment an effective amount of 4-hydroxypyridine derivative represented by the following formula (I):

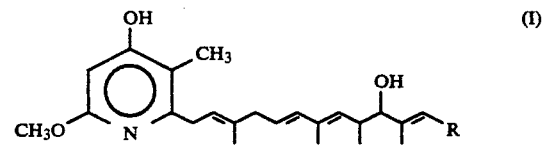

wherein R represents a methyl group or an isopropyl group.

3. The method according to claim 2 wherein the mammal is a human being.

4. The method according to claim 2 wherein the disease is hypertension.